(12) United States Patent
Van Rossum et al.

(10) Patent No.: US 11,913,949 B2
(45) Date of Patent: Feb. 27, 2024

(54) LATERAL FLOW MEMBRANE DESIGNED FOR MULTIPARAMETER READOUTS AND COMPACT MULTIPARAMETER LATERAL FLOW IMMUNOASSAY DEVICE COMPRISING THE SAME

(71) Applicant: Sartorius Stedim Biotech GmbH, Göttingen (DE)

(72) Inventors: Denise Van Rossum, Adelebsen (DE); Eric Jallérat, Ville d'Avray (FR); Susanne Drebing, Hardegsen (DE); Dieter Melzner, Göttingen (DE)

(73) Assignee: Sartorius Stedim Biotech GmbH (DE)

( * ) Notice: Subject to any disclaimer, the term of this patent is extended or adjusted under 35 U.S.C. 154(b) by 342 days.

(21) Appl. No.: 15/315,553

(22) PCT Filed: Apr. 28, 2015

(86) PCT No.: PCT/EP2015/000869
§ 371 (c)(1),
(2) Date: Dec. 1, 2016

(87) PCT Pub. No.: WO2015/188906
PCT Pub. Date: Dec. 17, 2015

(65) Prior Publication Data
US 2018/0143191 A1    May 24, 2018

(30) Foreign Application Priority Data
Jun. 10, 2014  (EP) .................................... 14290166

(51) Int. Cl.
*G01N 33/543* (2006.01)
*G01N 33/76* (2006.01)

(52) U.S. Cl.
CPC ....... *G01N 33/54388* (2021.08); *G01N 33/76* (2013.01); *B01L 2300/0883* (2013.01); *G01N 2333/59* (2013.01)

(58) Field of Classification Search
CPC .......... G01N 2035/00108; G01N 2035/00118; G01N 33/558; G01N 2035/00128;
(Continued)

(56) References Cited

U.S. PATENT DOCUMENTS 5,998,221 A * 12/1999 Malick ............. G01N 33/54366
422/401
9,970,933 B2 * 5/2018 Kim .................. G01N 33/56916
(Continued)

FOREIGN PATENT DOCUMENTS

DE     102007036906 A1    11/2008
EP          2031376 A2     3/2009
(Continued)

OTHER PUBLICATIONS

Translation for Apilux et al. (JP2012098237A) retrieved from Espacenet Patent Translate (https://worldwide.espacenet.com/patent/search/family/046390300/publication/JP2012098237A?q=in), 11 pages total (Year: 2012).*
(Continued)

*Primary Examiner* — Bao-Thuy L Nguyen
*Assistant Examiner* — Jennifer H. Tieu
(74) *Attorney, Agent, or Firm* — McDonald Hopkins LLC (57) ABSTRACT

The present invention relates to a multiparameter lateral flow strip (1), comprising a microporous membrane layer (2) supported on a liquid-impermeable support layer (3), for lateral flow of a liquid through the microporous membrane layer (2), wherein the microporous membrane layer (2) has two or more flow lanes (4) in the direction of lateral flow, wherein said two or more flow lanes (4) are separated by
(Continued)

hydrophobic separation channels (5), and wherein each of said two or more flow lanes (4) comprises a detection spot (6) including a binding agent, wherein said two or more flow lanes (4) are isomorphic lanes. Furthermore, the present invention relates to a multiparameter lateral flow immunoassay device comprising said multiparameter lateral flow membrane (1), the use of said multiparameter configured lateral flow membrane (1) in an immunological test, as well as to a method for the manufacture of said multiparameter configured lateral flow membrane (1).

18 Claims, 7 Drawing Sheets

(58) Field of Classification Search
CPC ....... G01N 2021/7759; G01N 21/8483; G01N 2021/8488; G01N 2021/8494; G01N 33/54386–54389; G01N 33/54388; Y10S 435/97; B01L 2300/0825; B01L 2300/0883
USPC ........................................................ 436/514
See application file for complete search history.

(56) References Cited

U.S. PATENT DOCUMENTS

| | | | | |
|---|---|---|---|---|
| 10,031,100 | B2* | 7/2018 | Johnson | B01L 3/5027 |
| 2006/0246599 | A1* | 11/2006 | Rosenstein | G01N 33/558 |
| | | | | 436/514 |
| 2007/0042444 | A1 | 2/2007 | Niskanen | |
| 2009/0298191 | A1* | 12/2009 | Whitesides | G01N 33/523 |
| | | | | 436/164 |
| 2011/0124130 | A1* | 5/2011 | Wagner | G01N 33/54366 |
| | | | | 436/518 |

FOREIGN PATENT DOCUMENTS

| | | | | | |
|---|---|---|---|---|---|
| JP | | 2012098237 A | * | 5/2012 | .......... G01N 33/543 |
| WO | WO-2013051890 A2 | * | 4/2013 | ....... G01N 33/54393 |

OTHER PUBLICATIONS

International Search Report and Written Opinion, prepared for PCT/EP2015/000869, dated Jul. 27, 2015.

* cited by examiner

LATERAL FLOW MEMBRANE DESIGNED FOR MULTIPARAMETER READOUTS AND COMPACT MULTIPARAMETER LATERAL FLOW IMMUNOASSAY DEVICE COMPRISING THE SAME

This application is a 35 U.S.C. 371 national stage filing and claims priority to PCT Application No. PCT/EP2015/000869, entitled "Lateral flow membrane designed for multiparameter readouts and compact multiparameter lateral flow immunoassay device comprising the same," filed Apr. 28, 2015, which claims the benefit of European Application No. 14290166.9, entitled "Lateral flow membrane designed for multiparameter readouts and compact multiparameter lateral flow immunoassay device comprising the same" filed Jun. 10, 2014, both of which are incorporated by reference herein in their entirety.

The present invention relates to a multiparameter lateral flow membrane comprising separated isomorphic flow lanes, and to a multiparameter lateral flow immunoassay device comprising the same.

In modern biochemical analytics, immunoassays are routinely used to detect the presence or concentration of various substances, often referred to as ligands or analytes, in biological fluids such as blood, urine or saliva but also in a variety of other samples for example food extracts, surface water and else. In a solid phase immunoassay, a binding agent, typically an antibody which is specific for the ligand to be detected, is immobilized on a solid support. A test fluid that may comprise the ligand to be detected is contacted with the solid support and a complex between the binding agent and the ligand is formed in case the ligand is present. In order to make the complex visible, labeled antibodies, may be used that bind to the complex followed by visual detection of the labeled antibody bound to the complex. Alternatively, an immunoassay is put together with a readout following a competitive reaction. To do so, the analyte per se is immobilized on a solid support and competes for the binding of the conjugated antibody with the analyte present in the sample. A sample rich in the defined analyte leads to a low absolute signal at the test line.

Porous materials such as nitrocellulose, nylon, cellulose acetate, glass fibers and other porous polymers have been employed as solid supports in solid phase immunoassays. In so-called lateral flow assays, a fluid to be tested for the presence of a ligand is applied to one end of a porous membrane layer and flows in lateral direction through the membrane under the action of capillary forces. The porous membrane comprises an immobilized binding agent that is capable of binding the ligand or the antibody against the ligand to be detected. The immobilized binding agent may be evenly distributed over the entire membrane. Typically, however, the immobilized binding agent is located in defined test or detection zones in the membrane, usually in narrow test lines that have been applied by means of contact or inkjet printing or other dispensing techniques.

In a lateral flow test, a thin layer of microporous material (membrane) with immobilized binding agent is supported on a liquid-impermeable layer to provide sufficient rigidity to the fragile microporous material layer. Usually a layer of microporous material with a thickness in the range of from about 80 to 200 μm is supported on a liquid-impermeable support layer, usually referred to as "membrane backing".

Furthermore, a lateral flow immunoassay device, typically in the form of a test strip, includes, in the direction of lateral flow, a prefilter pad, a conjugate pad, a lateral flow membrane as described above, and an adsorbent pad. In order to carry out a test with such a lateral flow immunoassay device, a liquid sample containing the ligands or analytes, which presence or concentration needs to be assessed, is dropped at one end of the lateral flow immunoassay device on the prefilter pad. The liquid sample will then migrate through capillary forces sequentially through the conjugate pad, the lateral flow membrane and finally into the adsorbent pad. During the migration, the ligands or analytes will react with conjugate particles present in the conjugate pad and then with a capture molecule, usually an antibody, which has been previously dispensed onto the membrane as a test or detection zone, typically in the form of a line oriented orthogonal to the direction of lateral flow.

The first lateral flow test strips capable to carry out a test with regard to one ligand or analyte have been developed in the 1980's. Since then, no major changes of said test format have been carried out, since it is rather cheap and compatible with mass production.

In order to accommodate the need for testing multiple ligands or analytes (parameters) in a liquid sample with one test strip, lateral flow test strips or devices including more than one test line have been developed.

However, said lateral flow test strips having multiple test lines are limited in the number of test lines (usually, only a maximum of 7 test lines is possible), since the moving speed of the liquid sample decreases at square of distance from the origin, the nature of the sample is frequently modified in an unpredictable manner when passing through multiple previous test lines, and the conjugate is depleted the longer the sample migrates through the test strip, such that a loss of sensitivity occurs.

A further concept of testing a plurality of ligands or analytes is shown in U.S. Pat. No. 7,879,597, which discloses a system including test cells with a first sorbent material defining a first flow path for a solution, a second sorbent material defining a second flow path distinct from the first flow path for a sample, and a test site with immobilized antigens or antibodies or other ligand binding molecules located at the junction of the first and second sorbent materials for identifying one or more ligands.

Although the system disclosed in U.S. Pat. No. 7,879,597 allows for up to 8 lines in parallel, said system still has some limitations and much higher production costs compared to single parameter lateral flow test strips.

Furthermore, in order to achieve a higher sensitivity for the ligands or analytes to be tested, other test formats have been developed. In this context, a major path of research consisted in reducing the volume of the test line in order to increase the number of conjugate particles per volume unit.

However, none of these trials resulted in a significant sensitivity increase due to the increased shear in the sample flow generated by these membrane volume and shape modifications.

In addition, as shown in U.S. Pat. No. 8,486,717 which relates to lateral flow devices using two-dimensional features, it is difficult to position different test zones (either lines or spots) in the same lateral flow device (strip), as the first test zones in the flow will deplete too much the sample from the conjugate particles. Furthermore, the other test zones need to be placed further apart, such that there is sufficient time for the sample flow to be again homogenized.

Thus, it is evident from the above that assessing several ligands or analytes with one lateral flow membrane, while keeping the ease of manufacturing of existing lateral flow test and simultaneously increase sensitivity, is a difficult task.

US 2007/0042444 A1 describes an immunodiffusion-based test device comprising a porous carrier material, wherein a specific binding reagent (immunoreagent) is applied in the form of a zone or a blot, a detectable label, whereto a second specific binding reagent is coupled, and which is supplied separately or pre-applied to the porous carrier, is mobilizable by the sample, and a sample application site optionally provided with a filter, characterized in that it comprises in the porous carrier material a network of channels, which is formed by etching porous carrier material with laser treatment, which network of channels comprises two or more channels separated by a treated area, one or more specific binding reagents immobilized in them, an optional label site placed in the channel near the sample application site, or in the sample application site itself, which is placed in a manner that enables an even distribution of the sample into each channel. EP 2 031 376 discloses an assay device for determining the presence and/or extent of one or more analytes in a liquid sample comprising a) first and second assays each comprising a flow-path having a detection zone for immobilising a labelled binding reagent, wherein detection of a labelled binding reagent at one or both detection zones is indicative of the presence and/or extent of one or more analytes, b) a shared reference zone, c) one or more light sources to illuminate the detection zones and the reference zone, d) one or more photodetectors to detect light from the detection zones and the reference zone, which photodetector/s generate a signal, the magnitude of which signal is related to the amount of light detected, and e) signal processing means for processing signals from the photodetector/s. US 2006/0246599 A1 describes a lateral flow device comprising a single membrane supporting a plurality of immunoassay modules arranged generally parallel to each other in a side-by-side relationship to operate independently of each other, each module extending generally parallel relative to a longitudinal axis of the lateral flow device and configured with a second fluid flow direction that is generally parallel to a first fluid flow direction of the single membrane, the first fluid flow direction extending generally parallel to the longitudinal axis of the lateral flow device. DE 10 2007 036 906 discloses a method for manufacturing a test strip for carrying out analysis by thin layer chromatography, wherein the test strip has at least two separation lanes for the fluid to be analyzed, wherein the separation lanes are formed of a microporous material, which is applied on a carrier in a structured manner, characterized in that a planar extending thin layer of a microporous material applied on the carrier in a thickness of less than 500 micrometers is structured by specific application of a hydrophobic substance, wherein the hydrophobic substance is liquid when applied and penetrates the thin layer, wherein the substance solidifies after the penetration and wherein regions being free of the substance form the separation lanes. U.S. Pat. No. 5,998,221 describes a process for assaying for an analyte in a sample, said process comprising providing a solid support having at least two lanes wherein each lane has a contact zone for applying sample to each lane and further wherein the first lane of the solid support has binder immobilized on the entire length of the first lane of the solid support, said binder being a binder for at least the analyte, and the second lane of the solid support is juxtaposed to the first lane of the solid support, and said second lane has binder immobilized on the entire length of said second lane of the solid support, said binder being a binder for at least the analyte, and a known amount of said analyte is immobilized on said binder which is immobilized on the entire length of the second lane of the solid support, contacting the contact zone of the first lane with sample and tracer wherein said tracer is comprised of a ligand labeled with a visible label, contacting the contact zone of the second lane with tracer, and determining the visibility of tracer bound in the first and second lanes of binder as a measure of analyte in the sample.

Accordingly, the object underlying the present invention is to provide a lateral flow membrane being capable of testing multiple ligands or analytes (parameters) in a liquid sample, and having an improved assay sensitivity and signal intensity, and to provide a corresponding manufacturing method.

It has now been found that the above object can be achieved by providing a multiparameter lateral flow membrane having two or more isomorphic flow lanes in the direction of lateral flow separated by hydrophobic separation channels, each lane comprising a detection zone or spot with a binding agent, whereby both the assay sensitivity can be improved and signal intensity of lateral flow immunoassays can be largely enhanced and multiple markers (parameters) in a liquid sample can be tested with one lateral flow membrane.

Accordingly, the present invention relates to a multiparameter lateral flow membrane, comprising a microporous membrane layer which may be supported or not on a liquid-impermeable support layer for lateral flow of a liquid through the microporous membrane layer, wherein the microporous membrane layer has two or more isomorphic flow lanes in the direction of lateral flow, wherein said two or more isomorphic flow lanes are separated by hydrophobic separation channels, and wherein each of said two or more isomorphic flow lanes comprises a detection zone or spot including a binding agent, wherein said two or more flow lanes (4) are isomorphic lanes.

The lateral flow membrane configured for multiparameter readouts according to the present invention can advantageously be applied in a multiparameter lateral flow immunoassay device.

In a further aspect, the invention relates to the use of the above-described multiparameter lateral flow membrane in immunological-based tests.

In a still further aspect, the invention relates to a method for the manufacture of a multiparameter lateral flow membrane as described above, comprising the steps of:
(a) providing a lateral flow membrane, comprising a microporous membrane layer supported or not on a liquid-impermeable support layer, for lateral flow of a liquid through the microporous membrane layer,
(b) laser-etching of the microporous membrane layer to form hydrophobic separation channels, such that two or more isomorphic flow lanes are provided in the direction of lateral flow, and
(c) applying a detection zone or spot including a binding agent on each of said two or more isomorphic flow lanes.

In a still further aspect, the invention relates to a multiparameter lateral flow test with two or more isomorphic lanes with dedicated reaction zone and dedicated conjugate storing zone, upstream of the reaction zone.

Figure 1:
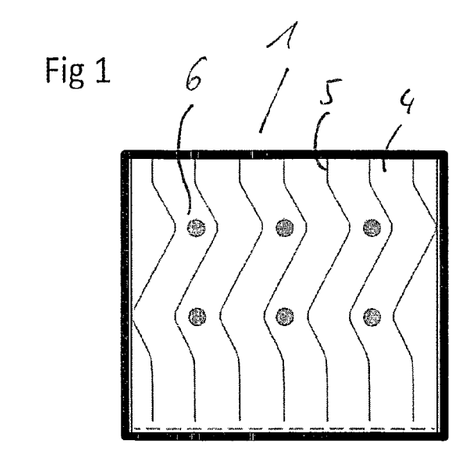
FIG. 1 shows a top view of a lateral flow membrane according to the present invention.
Figure 2:
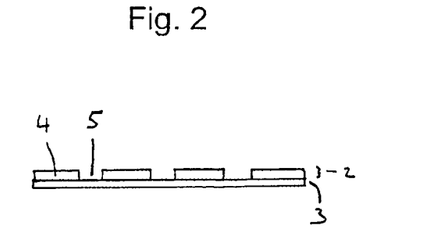
FIG. 2 shows a cross-sectional view of a lateral flow membrane according to the present invention in the lateral flow direction.
Figure 3:
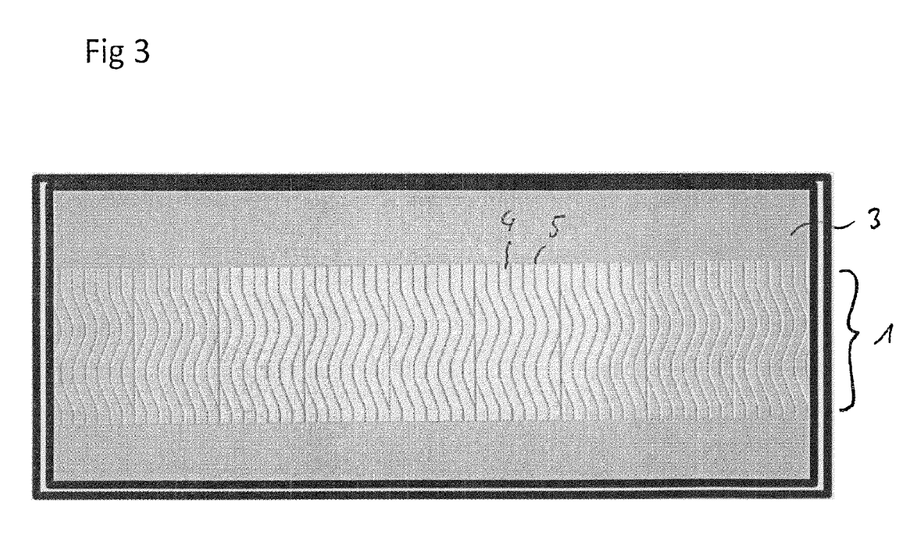
FIG. 3 shows a lateral flow membrane according to the present invention in the state after its lamination onto a backing card and before cutting to obtain single multiparameter strip. Alternatively, membranes structured for multiparameter readouts are processed in a roll format.

The multiparameter lateral flow membrane 1 according to the present invention as shown in FIG. 1 to 3 is an elongate arrangement of a microporous membrane layer 2 supported on a liquid-impermeable support layer 3. The multiparameter lateral flow membrane 1 is suitable for lateral flow of a liquid through the microporous membrane layer 2 under the action of capillary forces and is typically used in lateral flow immunoassays for detecting a ligand or analyte in a test fluid that flows laterally through the microporous membrane layer 2.

According to the present invention, the microporous membrane layer 2 has two or more isomorphic flow lanes 4 in the direction of lateral flow, as shown in FIGS. 1 and 2.

The width of the flow lanes 4 is not specifically restricted, however, is usually in the range of from 1 mm to 4 mm, preferably in the range of from 2 mm to 3 mm.

Furthermore, the shape of the flow lanes 4 is not specifically restricted. However, preferably, the shape of the flow lanes 4 is selected from the group consisting of straight lanes, zig-zag-shaped lanes and meander-shaped lanes. More preferably, the shape of the flow lanes is selected from the group consisting of zig-zag-shaped lanes and meander-shaped lanes, as shown in FIG. 1 (zig-zag-shaped lanes) and FIG. 3 (meander-shaped lanes).

Figure 5A:
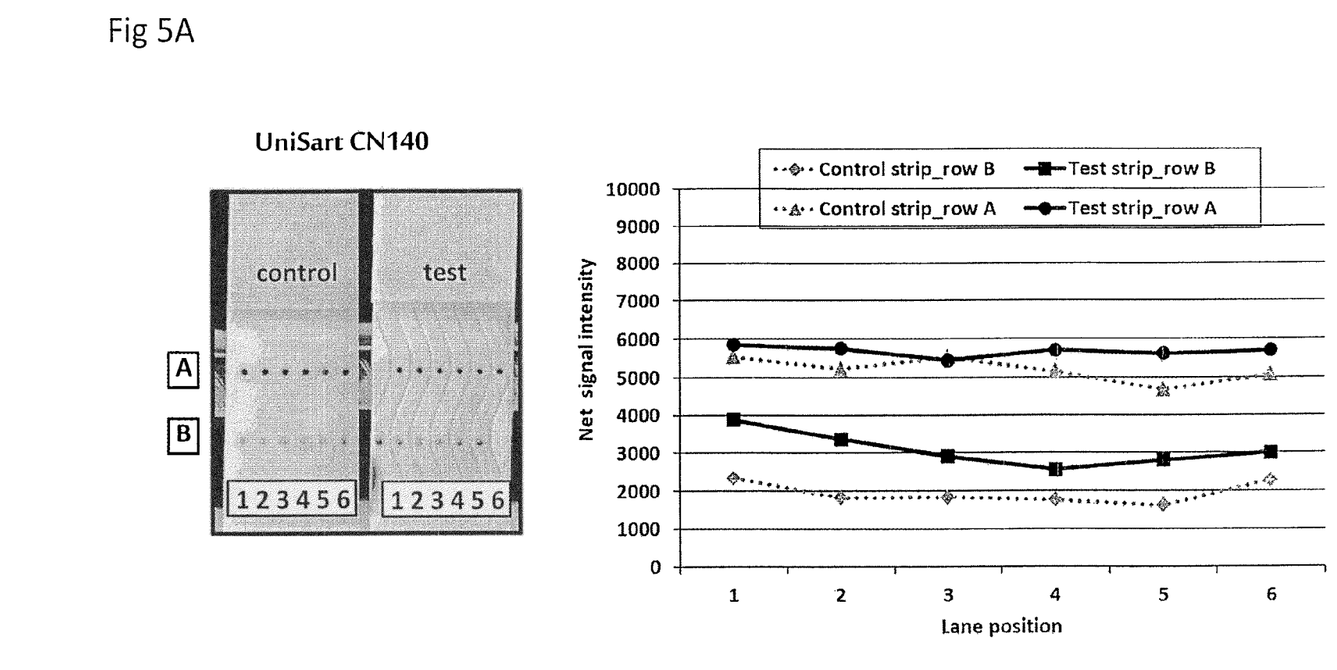
FIGS. 5A and 5B show the homogeneity of the sample flow through the whole width of the multiparameter lateral flow strip. Comparable signal intensities are observed in each individual lanes.
Figure 5B:
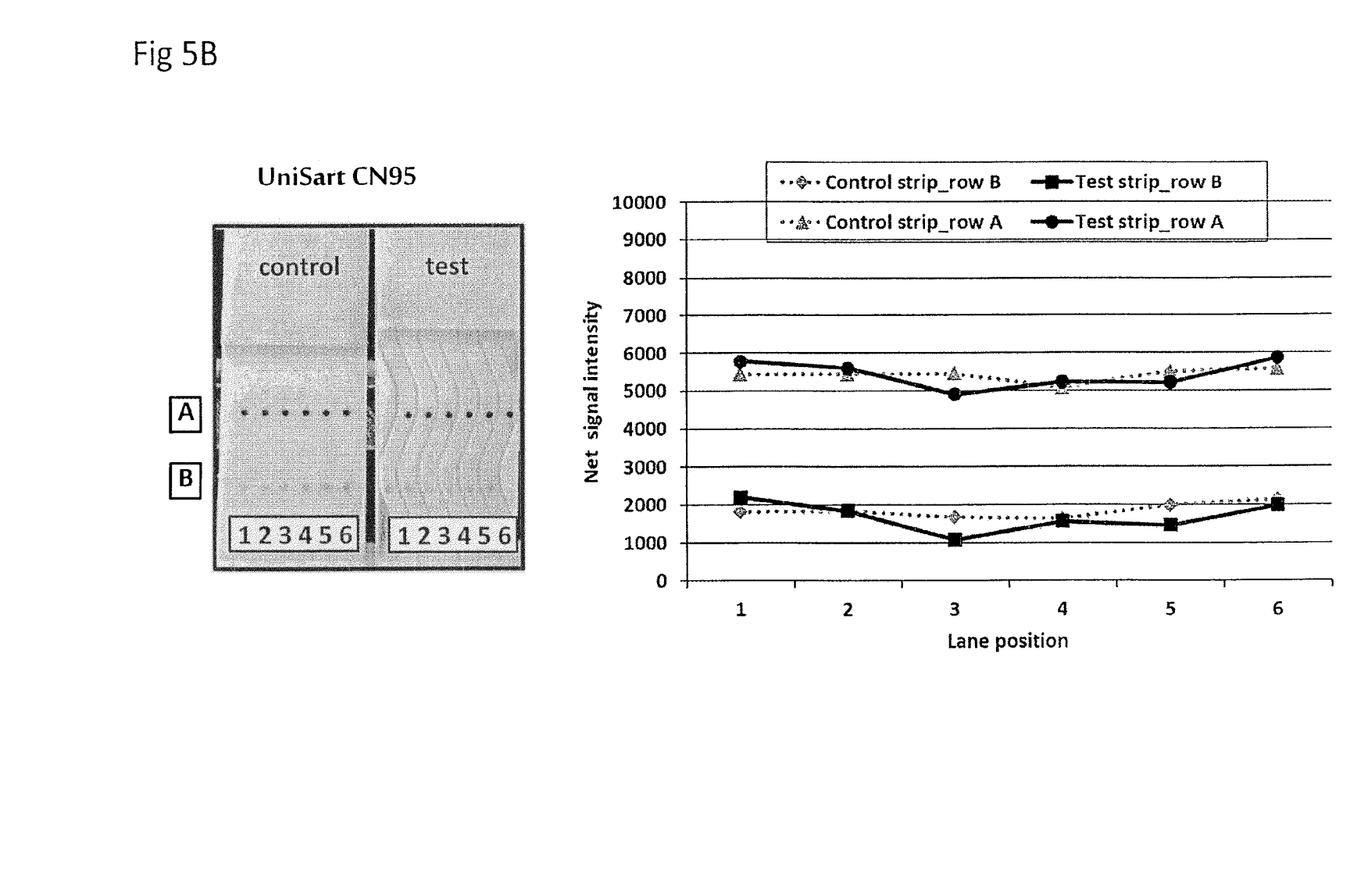

According to the present invention, the flow lanes 4 are separated by hydrophobic separation channels 5, as shown in FIG. 1 to 3, and each of said two or more isomorphic flow lanes 4 comprises a detection zone 6 including one binding agent, as shown for e.g. in FIG. 1, such that each detection zone 6 is supplied with the test liquid by its own flow lane. In one embodiment of the invention, each of the several flow lanes 4 can comprise a detection zone and at least some of the several flow lanes can comprise identical or different binding agent(s). Due to said separation, each detection zone (reaction zone) will receive exactly the same amount and the same quality of sample and conjugate solution, which results in an improved assay sensitivity and signal intensity for each detection spot 6 (FIG. 5).

According to a preferred embodiment of the present invention, each detection zone 6 has a diameter or dimension of from 0.5 mm to 3 mm, preferably of from 1 mm to 2 mm. Furthermore, the detection zone 6 preferably has a circular shape, but could also be in the shape of small lines (jetted non-contact spotting equipment).

According to a preferred embodiment of the present invention, the hydrophobic separation channels 5 have a width of from 0.1 mm to 1 mm, preferably from 0.15 mm to 1 mm.

The microporous membrane layer 2 may be made of any suitable microporous material for lateral flow membranes. Such materials are known in the art and include nitrocellulose, nylon, cellulose acetate, PES (polyethersulfone), PVDF (polyvinylidenfluoride), cross-linked dextran and other porous polymers. Preferably, the microporous membrane layer 2 is a nitrocellulose layer. Nitrocellulose membrane layers for lateral flow assays are well-known in the art and are composed of interconnected nitrocellulose rods-in-a-sponge like structure.

Liquid-impermeable support layers 3 are well-known in the art and are often referred to as "backing". Suitable support layers include polymeric materials such as for example polyester, polypropylene, polyethylene, acrylic (co)polymers, vinyl-acrylic polymers, polycarbonates and hetero-polysaccharides.

According to a preferred embodiment of the present invention, each of said two or more isomorphic flow lanes 4 further comprises a control zone (as shown in FIG. 5) including a binding agent downstream of the detection zone 6. Control zone of individual lanes can comprise different reagents. This control zone usually will bind all conjugate reagent or particle in excess.

The major role of the control zone is to assure that the liquid has been transported into the designated lane. The selected reagent combination will necessarily lead to a positive readout, independent of the outcome at the test zone. In FIG. 5, for example, an anti-mouse immunoglobulin purified from rabbit was printed at a final concentration of 1 mg/ml.

According to a preferred embodiment of the present invention, each control zone has a diameter or dimension in the same range as the test zone, i.e. from 0.5 mm to 3 mm, preferably of from 0.2 mm to 1.0 mm.

In order to visualize the complex between the binding agent and the ligand or analyte formed in the detection zones 6, detectable markers such as for example immunolabels are typically used. Most often, the liquid to be analyzed first flows through a so-called conjugate pad before it flows through the lateral flow membrane. The conjugate pad comprises a moveable conjugate of detectable marker and a detection agent, i.e. an agent that can bind to the ligand or analyte but different from the binding agent. If the liquid to be analyzed flows through the conjugate pad, the conjugate binds to the ligand and the ligand/conjugate complex flows with the liquid through the membrane layer. In the membrane layer the ligand-conjugate complex binds to the immobilized binding agent. The moveable conjugate is usually specific to one analyte. Consequently in a multiparameter test several conjugate reagents are mixed and applied on the conjugated pad through the whole pad width. Another option would be to spray the individual conjugated reagents at regular interval on the conjugated pad. The width of the interval corresponds to the width of the flow lanes resulting in a higher concentration of the desired conjugate in a specified lane. This option may also reduce the amount of conjugate necessary to generate a visible signal because of the higher reagent concentration for the defined areal. Alternative to a conjugate pad upstream of the lateral flow membrane, the lateral flow membrane per se may comprise at least one conjugate zone that comprises a moveable conjugate of detectable marker and detection agent. Such conjugate zones are located upstream of a detection spot. In this case only the conjugate specific to the ligand on the detection zone will flow in the dedicated lane without any loss in the other lanes. Suitable detectable markers that can be used in this respect are not particularly limited and are known in the art. They include for example latex beads of different colors or fluorescent dyes as well as gold nanoparticles.

Thus, according to a preferred embodiment of the present invention, each of said two or more isomorphic flow lanes 4 further comprises at least one conjugate spot that comprises a moveable conjugate of detectable marker and detection agent upstream of the detection spot 6. The membrane area used to deposit the conjugated reagent(s) can be slightly larger (0.5 mm) than the here defined isomorphic flow lane.

According to a preferred embodiment of the present invention, the binding agents are selected from the group consisting of proteins and peptides in particular antibodies and aptamers.

The present invention further relates to a lateral flow immunoassay device comprising the multiparameter lateral flow membrane according to the invention. Lateral flow immunoassay devices are well-known in the art and are for example described in US2006/0205059, U.S. Pat. Nos. 5,252,496 and 5,591,645. The multiparameter configured lateral flow membrane 1 according to the present invention may be used in any suitable lateral flow immunoassay device known in the art including in direct or competitive format.

Typically, the multiparameter lateral flow immunoassay device according to the present invention comprise a reaction zone comprising the multiparameter configured lateral flow membrane 1 according to the present invention, a sample addition zone upstream of the reaction zone and an absorbing zone downstream of the reaction zone. Test fluid is added to the sample addition zone that typically comprises a filter pad in which the liquid is absorbed. By the action of capillary forces, the liquid flows from the sample addition zone through the reaction zone to the absorbing zone. The device may comprise a so-called conjugate zone comprising moveable immunolabels or other markers that are conjugated to a detection agent that binds to the ligand of interest in the test liquid, between the sample addition zone and the reaction zone, so that test liquid is forced to flow through the conjugate zone. The labeled detection agents will then bind to the ligands in the test fluid and labeled ligands flow through the reaction zone and are bound to immobilized binding agents in the reaction zone where they can be visualized. Alternatively, the multiparameter configured lateral flow membrane 1 comprises at least one conjugate zone as described hereinabove.

According to the present invention, the method for the manufacture of the multiparameter lateral flow membrane 1 comprises the steps of
  (a) providing a lateral flow membrane, comprising a microporous membrane layer 2 supported or not on a liquid-impermeable support layer 3, for lateral flow of a liquid through the microporous membrane layer 2,
  (b) laser-etching of the microporous membrane layer 2 to form hydrophobic separation channels 5, such that two or more isomorphic flow lanes 4 are provided in the direction of lateral flow, and
  (c) applying a detection spot 6 including a binding agent on each of said two or more isomorphic flow lanes 4.

The lateral flow membrane provided in step (a) of the present method is a common lateral flow membrane, which can be manufactured in a known manner, typically by first providing a liquid-impermeable support layer 3 and then applying a solution of the material of which the microporous membrane layer 2 is composed in a suitable solvent on the support layer 3. The solvent is then evaporated and a lateral flow membrane of a microporous membrane layer 2 supported on the liquid-impermeable support layer 3 is obtained.

According to step (b) of the present method, laser-etching of the microporous membrane layer 2 to form hydrophobic separation channels 5 is carried out, such that two or more isomorphic flow lanes 4 are provided in the direction of lateral flow.

Specifically, the microporous membrane layer 2 is treated with laser-etching such that the material of the microporous membrane layer 2 is removed from the liquid-impermeable support layer 3 and a plurality of isomorphic flow lanes 4 is formed, which are separated by hydrophobic borderlines 5 reaching down to the exposed hydrophobic material of the liquid-impermeable support layer 3.

The laser etching process can be achieved for example by the use of a $Nd:YVO_4$ solid-state laser having picosecond pulses, especially at a wavelength of 532 nm and a pulse length of 12 psec, a pulse energy of 10 mJ and a pulse frequency of 10 kH. Alternative laser etching process with Nd YAG or $CO_2$ laser have also led to successful structuring of nitrocellulose membrane.

The product from step (b) can be processed into different formats. A preferred embodiment is a roll. Another preferred embodiments of such a format is a package of sheets.

According to step (c) of the present method, a detection spot 6 including binding agent(s) (identical or different) is applied on each of said two or more isomorphic flow lanes 4 with common techniques. Preferably, the detection spots 6 are applied by contact or inkjet printing or aerosol spraying.

Optionally, in a further step a conjugate zone that comprises a moveable conjugate of detectable marker and detection agent is applied upstream of the detection spots 6.

The present invention is further illustrated by the following examples, without being limited thereto.

EXAMPLES

Example 1: Preparation of a Lateral Flow Membrane Using an Evaporation Process

A nitrocellulose-based lateral flow membrane is manufactured by an established evaporation process. Briefly, a polymer blend solution of nitrocellulose (3 to 10% (wt)) with 30 to 50% (wt) of alcohol, 40 to 60% (wt) of methyl acetate, and 7 to 13% (wt) of water is applied on a stainless belt or on a polyester film. The casting line offers a controlled evaporation process of the volatile components. The resulting membrane is impregnated with an anionic surfactant to assure homogeneous capillary flow through the whole membrane thickness. The membrane is then dried, winded into final rolls and carefully examined for physical and chemical characteristics.

The ready to use lateral flow membrane is laminated onto backing card (G&L Precision Die Cutting) and structured by laser etching to allow for multiple individual reactions and readouts. The membrane segment of the backing card is then printed with protein solution with a high precision liquid dispenser such as sciFLEXarrayer (Scienion AG, Berlin) at the designated areas. The respective sample (Ahlstrom, Grade 6615), conjugate and absorbent pads (Ahlstrom; grade 222) are assembled onto the backing card. The final strip that includes 2 or more flow lanes are then cut off from the backing card.

Example 2: Multiparameter Lateral Flow Assay 1

A nitrocellulose membrane manufactured, laminated and mounted as in Example 1 is prepared. Half of the backing cards is structured with individual flow lanes, the other half is not. Forty millimeter wide strips are generated including 6 flow lanes and 1 test spot per lane or 6 test spots juxtaposed on the whole membrane areal but with an identical positioning as the structured lateral flow membrane strip. The test spots are applied with a non-contact dispensing system (sciFLEXarrayer, Scienion AG) and contains 50 nl anti-hCGα (anti-human chorionic gonadotropin-alpha, Arista Biological). Fifteen μl of a solution of anti-hCGβ-gold conjugated antibody (BBI International) in 100 mM Tris-HCl, pH 8.0 buffer is apposed on the conjugated pad of the strip.

Figure 4A:
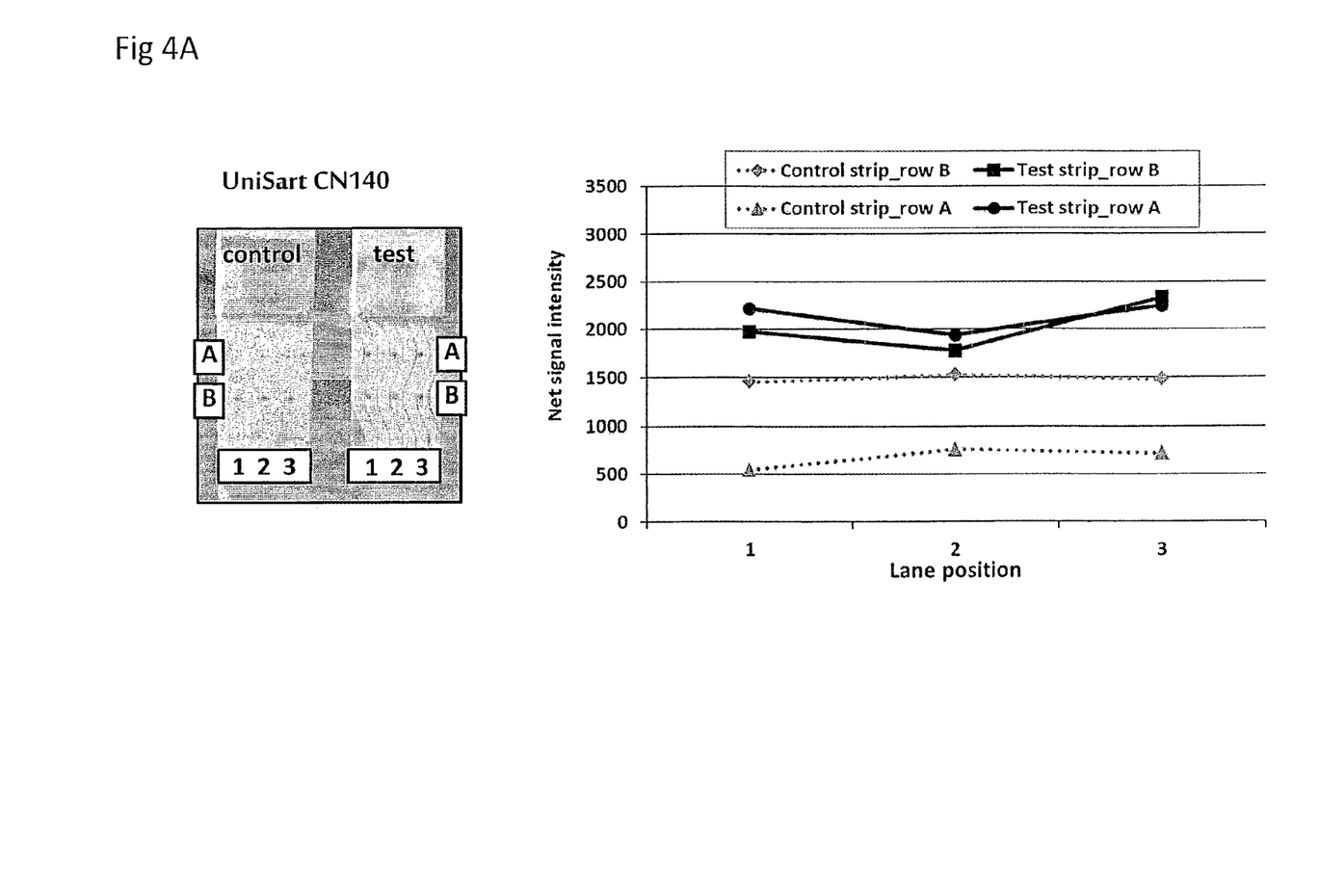
FIGS. 4A and 4B show the results of a signal intensity test of a lateral flow membrane according to the present invention compared with a UniSart lateral flow membrane using anti-hCG antibodies.
Figure 4B:
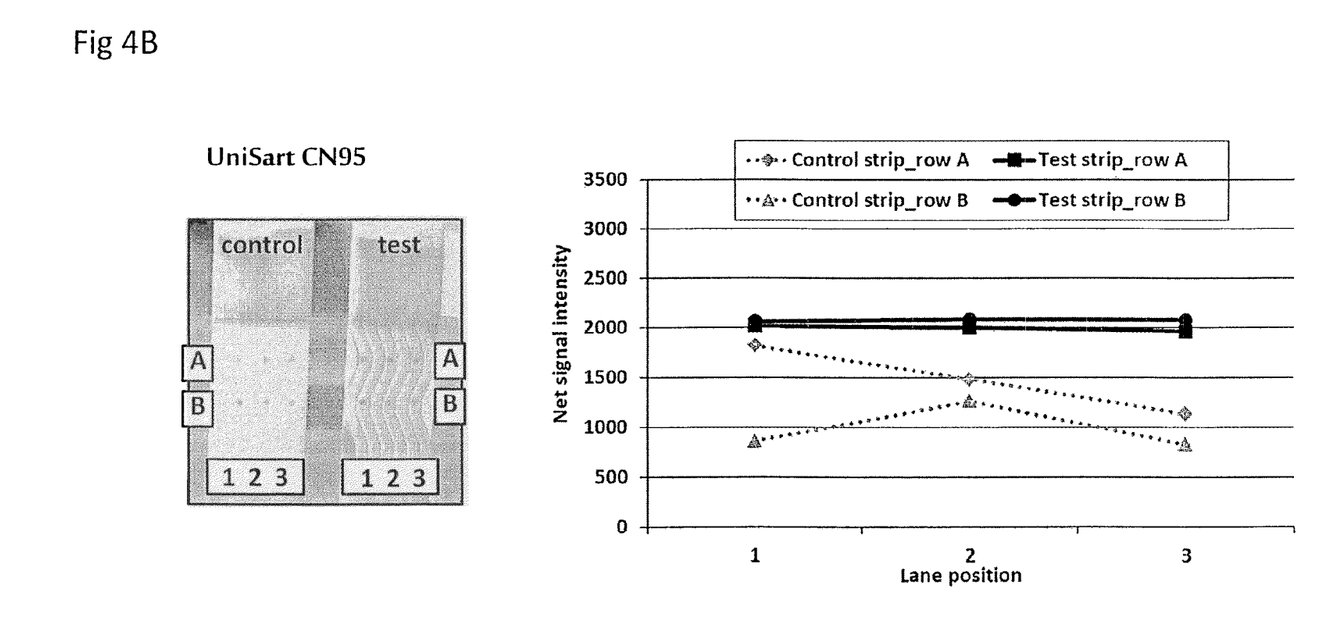

The lateral flow strips made with either nitrocellulose membrane UniSart 140 (FIG. 4A) or UniSart 95 (FIG. 4B) are incubated with a sample that includes 50 mIU hCG dissolved in 20 mM Tris buffer, 150 mM NaCl, 0.05% BSA, pH 8.2. The test strips are kept in an upright position until the liquid frontier line has reached ca. half the height of the absorbent pad (between 10 and 15 min). The test spots develop a dark red color. The latter is proportional to the amount of bound gold-conjugate. A digital picture of the strips is taken with a CCD camera (VersaDoc, BioRad) and the intensity of the respective test spots is quantified with Image Lab (FIG. 4A). Net signal intensity is reported here and is defined as the absolute signal intensity minus the intensity of the immediate background.

Example 3: Multiparameter Lateral Flow Assay 2

Lateral flow strips are prepared as described in Example 2 except for the fact that 2 spots (one test and one control spot) are applied in each flow lane. The control spots include a rabbit anti-mouse immunoglobulin (1 mg/ml, BBI international). The lateral flow tests are made with the UniSart CN 140 (FIG. 5A) or the UniSart CN 95 (FIG. 5B) nitrocellulose membrane. The 40 mm wide strips are cut from the backing cards and the respective conjugate pad treated with 15 μl of anti-hCGβ-gold conjugated antibody solution. The lateral flow strips are then incubated with 25 mIU hCG dissolved in 20 mM Tris buffer, 150 mM NaCl, 0.05% BSA, pH 8.2. A digital picture is recorded and the image analysed as described in Example 2.

The following reference signs are used in the present application:
1 Multiparameter lateral flow membrane
2 Microporous membrane layer
3 Liquid-impermeable support layer
4 Isomorphic flow lanes
5 Hydrophobic separation channels
6 Detection spot

The invention claimed is:

1. A multiparameter lateral flow membrane for testing multiple ligands or analytes in a liquid sample, comprising a microporous membrane layer for lateral flow of a liquid through the microporous membrane layer,
wherein the microporous membrane layer has two or more flow lanes in the direction of lateral flow, each of the flow lanes constituting a single, unitary flow lane
wherein said two or more flow lanes run parallel and adjacent to one another and are separated by hydrophobic separation channels, where adjacent flow lanes are exclusively separated by a shared hydrophobic separation channel over the length of the adjacent flow lanes, and
wherein each of said two or more flow lanes comprises a detection zone including a binding agent,
wherein said two or more flow lanes are isomorphic lanes,
wherein said two or more flow lanes are zig-zag-shaped lanes or meander-shaped lanes; and
wherein the detection zone in a first flow lane, and the detection zone in a second flow lane adjacent to the first flow lane are positioned along a common line in the direction of fluid flow.

2. The multiparameter lateral flow membrane according to claim 1, wherein the hydrophobic separation channels have a width of 0.15 mm to 1.5 mm.

3. The multiparameter lateral flow membrane according to claim 1, wherein the microporous membrane layer is made of nitrocellulose.

4. The multiparameter lateral flow membrane according to claim 1, wherein the binding agent is selected from the group consisting of antibodies or aptamers.

5. The multiparameter lateral flow membrane according to claim 1, wherein the detection zone has a dimension of from 0.5 mm to 3 mm.

6. The multiparameter lateral flow membrane according to claim 1, wherein each of said two or more isomorphic flow lanes further comprises a control zone downstream of the detection zone.

7. The multiparameter lateral flow membrane according to claim 6, wherein the control zone has a dimension of 0.5 mm to 3 mm.

8. The multiparameter lateral flow membrane according to claim 1, wherein each of said two or more flow lanes further comprises at least one conjugate zone that comprises a moveable conjugate of detectable marker and detection agent upstream of the detection zone.

9. A multiparameter lateral flow immunoassay device comprising the multiparameter lateral flow membrane according to claim 1.

10. A method of conducting an immunological test comprising adding a fluid to be tested to a immunoassay device comprising the multiparameter lateral flow membrane according to claim 1.

11. A method for the manufacture of a multiparameter lateral flow membrane according to claim 1, comprising the steps of:
(a) providing a lateral flow membrane, comprising a microporous membrane layer for lateral flow of a liquid through the microporous membrane layer,
(b) laser-etching of the microporous membrane layer to form hydrophobic separation channels, such that two or more isomorphic flow lanes are provided in the direction of lateral flow, the two or more isomorphic flow lanes run parallel and adjacent to one another, and the two or more isomorphic flow lanes are zig-zag-shaped lanes or meander-shaped lanes,
(c) optionally processing step (b) on a membrane roll, and
(d) applying a detection zone including one or more binding agents on each of said two or more low lanes.

12. The method according to claim 11, wherein the detection zones are applied by contact or inkjet printing or aerosol spraying.

13. A multiparameter lateral flow membrane, comprising a microporous membrane layer for lateral flow of a liquid through the microporous membrane layer,
wherein the microporous membrane layer has at least two flow lanes in the direction of lateral flow, including a first flow lane and a second flow lane, the first flow lane and the second flow lane each defining a single, unitary, flow lane,
wherein each of said at least two flow lanes comprises a detection zone including a binding agent, wherein a shared, single hydrophobic separation channel exclusively separates said first flow lane from said second flow lane over the length of the first flow lane and the second flow lane, wherein said at least two flow lanes are isomorphic lanes, wherein said at least two flow lanes are zig-zag-shaped lanes or meander-shaped lanes; and wherein the detection zone in a first flow lane, and the detection zone in a second flow lane adjacent to the first flow lane are positioned along a common line in the direction of fluid flow.

14. The multiparameter lateral flow membrane of claim 13, wherein said hydrophobic separation channel is formed from the exposure of a liquid-impermeable support layer.

15. The multiparameter lateral flow membrane of claim 13, wherein said hydrophobic separation channel is formed by laser etching.

16. The multiparameter lateral flow membrane of claim 13, wherein said single hydrophobic separation channel separates said first flow lane from said second flow lane along the entire length of said first flow lane and said second flow lane.

17. The multiparameter lateral flow membrane of claim 1, wherein the two or more flow lanes comprise (i) a first pair of flow lanes comprising a first flow lane and a second flow lane adjacent to the first flow lane, each of the first and second flow lane having detection zone, wherein the detection zone in the first flow lane, and the detection zone the a second flow lane adjacent to the first flow lane are positioned along a common line in the direction of fluid flow; and (ii) a second pair of flow lanes adjacent to the first pair of flow lanes, the second pair of flow lanes comprising a third flow lane and a fourth flow lane adjacent to the third flow lane, each of the third and fourth flow lane having detection zone, wherein the detection zone in the third flow lane, and the detection zone in the fourth flow lane adjacent to the third flow lane are positioned along a common line in the direction of fluid flow.

18. The multiparameter lateral flow membrane of claim 17, wherein the detection zone of the first flow lane of the first pair and the detection zone of the third flow lane of the second pair are positioned on a common line orthogonal to the direction of fluid flow, and the detection zone of the second flow lane of the first pair and the detection zone of the fourth flow lane of the second pair are positioned on a common line orthogonal to the direction of fluid flow.

* * * * *